United States Patent
DiMatteo et al.

(10) Patent No.: US 7,179,283 B2
(45) Date of Patent: Feb. 20, 2007

(54) VAPOR DEPOSITION PROCESS FOR PRODUCING A STENT-GRAFT AND A STENT-GRAFT PRODUCED THEREFROM

(75) Inventors: Kristian DiMatteo, Waltham, MA (US); Robert C. Thistle, Brockton, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 388 days.

(21) Appl. No.: 10/003,149

(22) Filed: Nov. 2, 2001

(65) Prior Publication Data

US 2003/0093141 A1   May 15, 2003

(51) Int. Cl.
*A61F 2/06* (2006.01)
(52) U.S. Cl. .................................... 623/1.13
(58) Field of Classification Search ............... 623/1.13, 623/1.42–1.43, 1.46; 606/191, 194
See application file for complete search history.

(56) References Cited

U.S. PATENT DOCUMENTS

| | | | |
|---|---|---|---|
| 3,246,627 A | | 4/1966 | Loeb et al. |
| 3,405,117 A | | 10/1968 | Yeh |
| 4,734,300 A | | 3/1988 | Simanyi et al. |
| 4,863,762 A | | 9/1989 | Aramaki et al. |
| 4,945,856 A | | 8/1990 | Stewart |
| 5,078,091 A | | 1/1992 | Stewart |
| 5,258,042 A | * | 11/1993 | Mehta .......................... 600/36 |
| 5,268,033 A | | 12/1993 | Stewart |
| 5,383,928 A | | 1/1995 | Scott et al. |
| 5,395,390 A | | 3/1995 | Simon et al. |
| 5,464,450 A | * | 11/1995 | Buscemi et al. .............. 623/1.2 |
| 5,609,629 A | | 3/1997 | Fearnot et al. |
| 5,637,113 A | | 6/1997 | Tartaglia et al. |
| 5,669,930 A | * | 9/1997 | Igarashi ....................... 606/191 |
| 5,700,286 A | | 12/1997 | Tartaglia et al. |
| 5,716,410 A | | 2/1998 | Wang et al. |
| 5,779,732 A | | 7/1998 | Amundson |
| 5,824,049 A | | 10/1998 | Ragheb et al. |
| 5,834,005 A | | 11/1998 | Usala |
| 5,873,904 A | | 2/1999 | Ragheb et al. |
| 5,882,725 A | | 3/1999 | Radford |
| 5,922,339 A | * | 7/1999 | Usala .......................... 424/424 |
| 6,096,070 A | | 8/2000 | Ragheb et al. |
| 6,156,435 A | | 12/2000 | Gleason et al. |
| 6,290,720 B1 | * | 9/2001 | Khosravi et al. ........... 623/1.13 |
| 6,673,102 B1 | * | 1/2004 | Vonesh et al. ............. 623/1.13 |
| 6,695,833 B1 | * | 2/2004 | Frantzen .................... 623/1.13 |
| 2003/0082323 A1 | * | 5/2003 | Venditti et al. ............ 428/36.9 |
| 2003/0082324 A1 | * | 5/2003 | Sogard et al. ............. 428/36.9 |

FOREIGN PATENT DOCUMENTS

EP         0351584 A1 *   1/1990

(Continued)

*Primary Examiner*—Tan-Uyen T. Ho
(74) *Attorney, Agent, or Firm*—Hoffmann & Baron LLP

(57) ABSTRACT

A stent-graft endoprosthesis is provided. The graft is a non-textile graft made from biocompatible polymers. The biocompatible compatible polymers include poly-para-xylylene polymeric material. The stent is also coated with a poly-para-xylylene polymeric material. The graft is formed by vacuum vapor deposition of diradicals forming the poly-para-xylylene material. The stent is also coated with the poly-para-xylylene material by vacuum vapor deposition.

29 Claims, 5 Drawing Sheets

FOREIGN PATENT DOCUMENTS

| | | |
|---|---|---|
| EP | 0 679 373 A2 | 11/1995 |
| EP | 0 716 834 A1 | 6/1996 |
| WO | WO 97/07257 | 2/1997 |
| WO | WO 97/15699 | 5/1997 |
| WO | WO 97/15951 | 5/1997 |
| WO | WO 98/17331 | 4/1998 |
| WO | WO 98/36784 | 8/1998 |
| WO | WO 00/04204 | 1/2000 |
| WO | WO 00/10622 | 3/2000 |

* cited by examiner

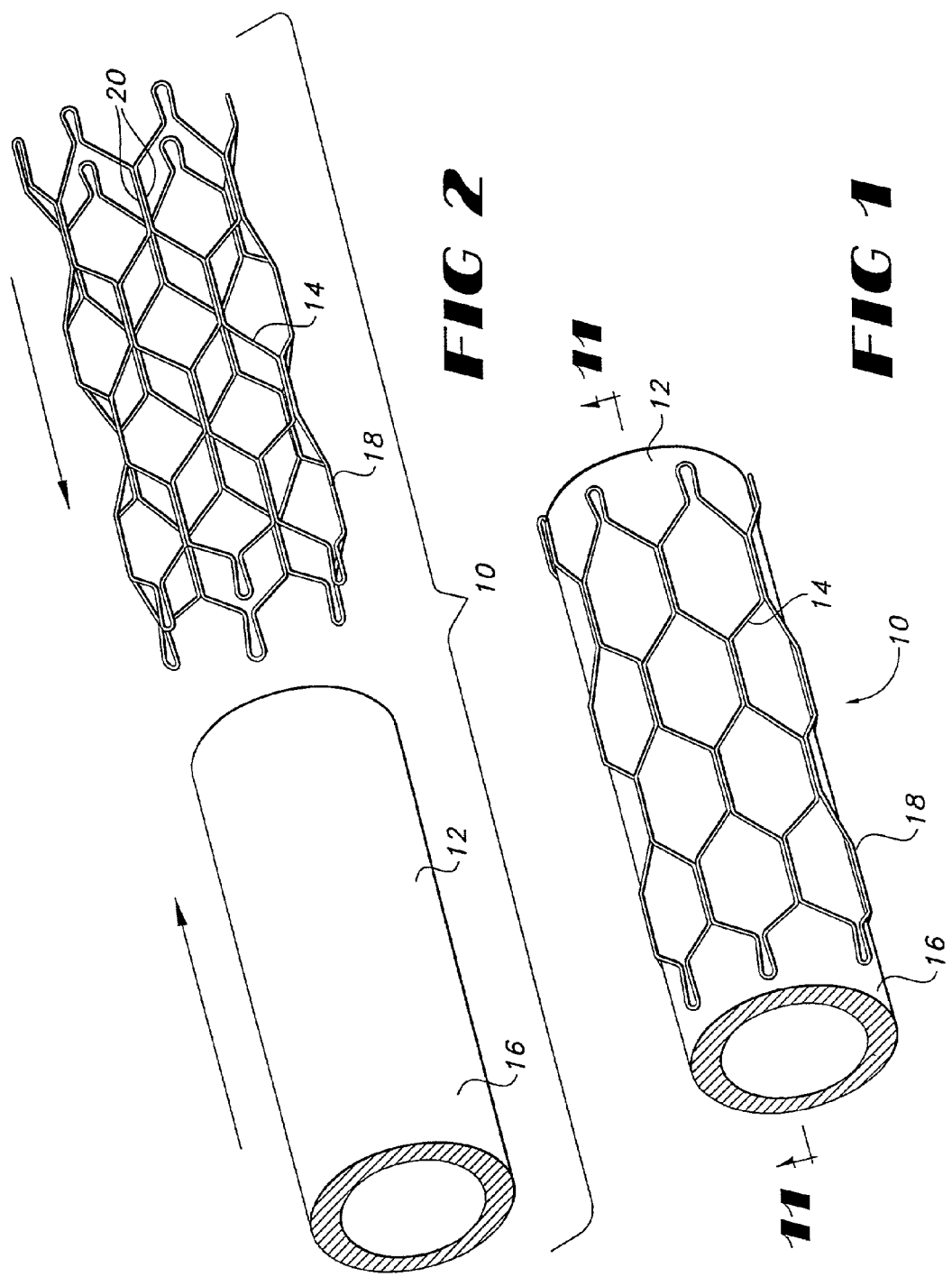

VAPOR DEPOSITION PROCESS FOR PRODUCING A STENT-GRAFT AND A STENT-GRAFT PRODUCED THEREFROM

FIELD OF INVENTION

The present invention relates generally to a tubular implantable prosthesis having a polymeric tubular structure. More particularly, the present invention relates to a stent-graft endoprosthesis having increased biocompatibility and mechanical strength with a tubular structure formed by vapor deposition of a poly-para-xylylene material.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures and aneurysms in various blood vessels. These devices are implanted within the vessel to open and/or reinforce collapsing or partially occluded sections of the vessel.

Stents generally include an open flexible configuration. This configuration allows the stent to be inserted through curved vessels. Furthermore, this configuration allows the stent to be configured in a radially compressed state for intraluminal catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Structures which have been used as intraluminal vascular grafts have included coiled stainless steel springs; helically wound coil springs manufactured from a heat-sensitive material; and expanding stainless steel stents formed of stainless steel wire in a zig-zag pattern. Examples of various stent configurations are shown in U.S. Pat. No. 4,503,569 to Dotter; U.S. Pat. No. 4,733,665 to Palmaz; U.S. Pat. No. 4,856,561 to Hillstead; U.S. Pat. No. 4,580,568 to Gianturco; U.S. Pat. No. 4,732,152 to Wallsten; U.S. Pat. No. 5,395,390 to Simon et al. and U.S. Pat. No. 4,886,062 to Wiktor, all of whose contents are incorporated herein by reference.

A graft is another commonly known type of intraluminal prosthesis which is used to repair and replace various body vessels. A graft provides a lumen through which blood may flow. Moreover, a graft is often configured as being generally impermeable to blood to inhibit substantial leakage of blood therethrough. Grafts are typically hollow tubular devices that may be formed of a variety of materials, including textile and non-textile materials.

A stent and a graft may be combined into a stent-graft endoprosthesis to combine the features thereof. It is often desirable to use a thin-walled graft in the stent-graft endoprosthesis to minimize the profile of the endoprosthesis and to maximize the flow of blood through the endoprosthesis. In such cases non-textile materials, such as polymeric tubes or sheets, are often used. Expanded polytetrafluoroethylene or e-PTFE is one common polymeric material used as the graft portion of a stent-graft endoprosthesis. Expanded polytetrafluoroethylene grafts, however, are subject to tearing or puncturing, leaving the stent-graft endoprosthesis prone to leakage of blood therethrough. Furthermore, expanded polytetrafluoroethylene grafts are susceptible to kinking, which is also undesirable because it may lead to poor blood flow patterns.

Thus, there is a need for a polymeric graft for use in a stent-graft endoprosthesis that has improved mechanical properties to resist tearing or puncturing.

SUMMARY OF THE INVENTION

The present invention provides an implantable tubular prosthesis or a stent-graft endoprosthesis having a seamless tubular graft of biocompatible polymeric material and a radially expandable coated stent securably disposed over an exterior surface of the graft. The coated stent is coated with the same said biocompatible polymeric material from which the graft is made of. The biocompatible polymeric material is poly-para-xylylene material.

In another aspect of the present invention an implantable stent-graft device is provided. The device includes a seamless and self supporting non-textile tubular graft of biocompatible polymeric material having a wall thickness of about 10 microns to about 100 microns and a radially expandable stent securably disposed over portions of the exterior surface of the graft.

In yet another aspect of the present invention a stent-graft endoprosthesis is provided. The endoprosthesis includes a seamless tubular non-textile graft of biocompatible polymeric material having a wall thickness of about 10 microns to about 250 microns and a radially expandable stent securably disposed over portions of the exterior surface of the graft. The polymeric material is a poly-para-xylylene material.

A method for producing the implantable devices of the present invention includes providing a mandrel having a cylindrical outer surface; depositing a poly-para-xylylene polymer onto a portion of the outer surface of the mandrel to form a tubular polymeric graft; providing a radially expandable stent; and securing portions of the stent to portions of the outer surface of the graft to form said stent-graft endoprosthesis. The method further includes vacuum vapor depositing of selected diradicals to form the poly-para-xylylene polymer.

BRIEF DESCRIPTION OF THE DRAWINGS

FIG. 1 is a perspective view of a stent-graft of the present invention.

FIG. 2 is an exploded view of the stent-graft of FIG. 1.

DETAILED DESCRIPTION OF THE INVENTION

Figure 3:
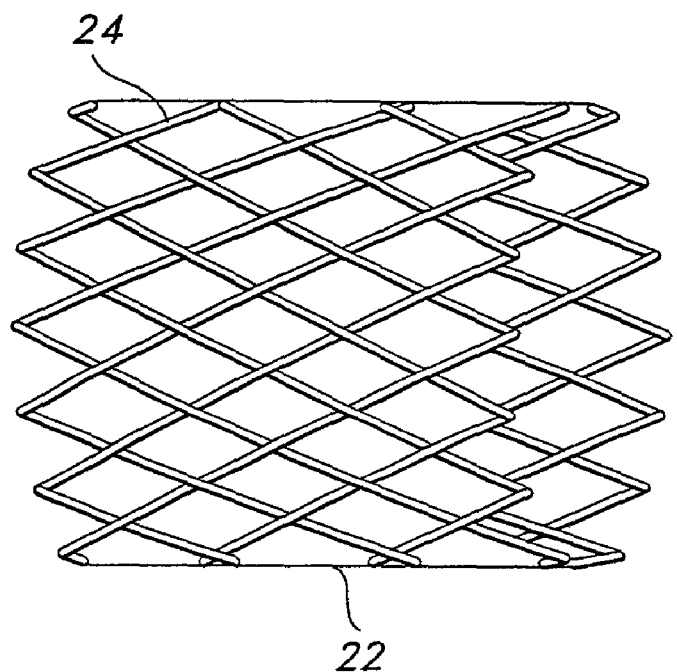
FIG. 3 depicts a wire stent of the present invention.

The present invention addresses the problems associated with prior art stent-graft endoprostheses. The present invention includes a stent-graft endoprosthesis having a polymeric graft or liner to reduce its overall profile as compared to, for example, textile grafts. Moreover the polymeric material is a poly-para-xylylene material which is not only biocompatible but also has improved mechanical characteristics over the more commonly used polytetrafluoroethylene materials. Furthermore, the polymeric graft portions of the present invention are non-porous which inhibits cellular attachment, minimizes thrombus adherence and reduces turbulence to flow.

Various stent types and stent constructions may be employed in the invention. Useful stents include, without limitation, self-expanding stents and balloon expandable stents. The stents may be capable of radially contracting or expanding, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode, based on temperature. Other materials are of course contemplated, such as stainless steel, platinum, gold, titanium, tantalum and other biocompatible metals, including alloys, such as Elgiloy®, a Ni—Co—Cr based alloy, as well as polymeric stents.

A stent-graft endoprosthesis 10 of the present invention is depicted in FIGS. 1 and 2. The endoprosthesis 10 includes a stent 14 and a non-textile graft 12. The graft 12 and the stent 14 are both tubular structures. Stent 14 is circumferentially and axially disposed on the outer surface 16 of the graft 12. As such graft 12 acts as an interior liner for endoprosthesis 10. The inner diameter of stent 14 is larger than the nominal diameter of graft 12 to permit the sliding of stent 14 over graft 12 as depicted in FIG. 2. Furthermore, as depicted in FIG. 2 graft 12 is a self-supporting graft. In other words graft 12 has a substantially tubular shape and maintains such a shape even without securement to the stent 14.

Moreover, graft 12 is a non-textile graft. As used herein textile and its variants refer to a structure of interlocked fibers formed by weaving, knitting, braiding or the like, and a "textile material" refers to a natural or synthetic fiber which can be woven, knitted, braided or the like into a textile graft. As used herein, non-textile and its variants refer to a structure formed by non-textile methods, such as extruding, molding, depositing, solidifying, polymerizing of materials. Non-textile structures include, but are not limited to, sheets, tubes, rods, blocks and other three-dimensionally shaped structures.

As shown in FIG. 2 stent 14 is a generally tubular structure having an open lattice structure. Stent wire 18 is generally configured a mesh of a plurality of interconnected cells of polygonal configuration. Desirably, the polygonal configurations are hexagonal. The cells may be interconnected by any convenient means. Desirably, the cells are welded together at portions of the straight segments 20.

The present invention, however, is not limited to a stent having a plurality of interlocking polygonal cells. The configuration of stent 14 may be of any suitable geometry. As shown in FIG. 3, wire stent 22 is a hollow tubular structure formed from wire strand 24 being arranged in what can be described as a "Z" or a "zig-zag" pattern. Wire strand 24 may be formed by, for example, braiding or spinning it over a mandrel. Alternatively, wire stent 24 may be formed from more than one wire strand. Wire stent 22 is capable of being radially compressed (not shown) for implantation into a bodily lumen.

Figure 4:
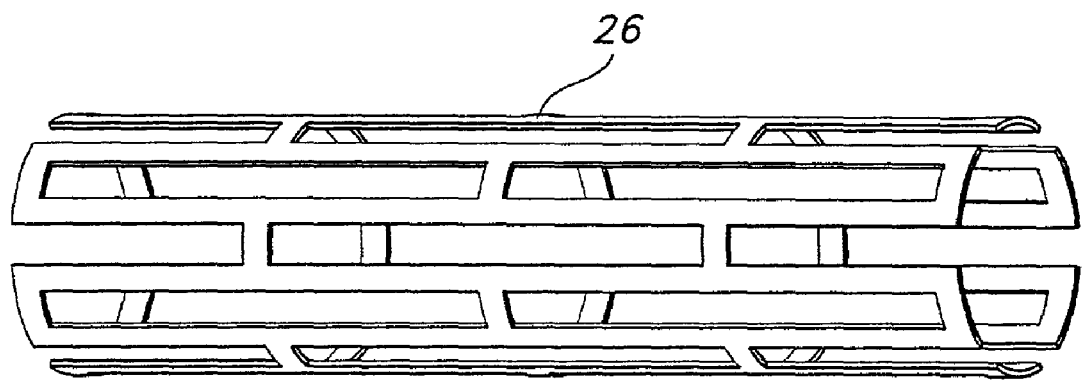
FIG. 4 depicts a slotted stent of the present invention.

In another aspect of the present invention, a slotted stent 26 is also useful as part of the stent-graft 10. As depicted in FIG. 4, slotted stent 26 is suitably configured for implantation into a bodily lumen (not shown). Upon locating the slotted stent 26 at the desired bodily site, slotted stent 26 is radially expanded (not shown) for securement at the desired site. The slotted stent 36 may also be self-expanding.

Figure 5:
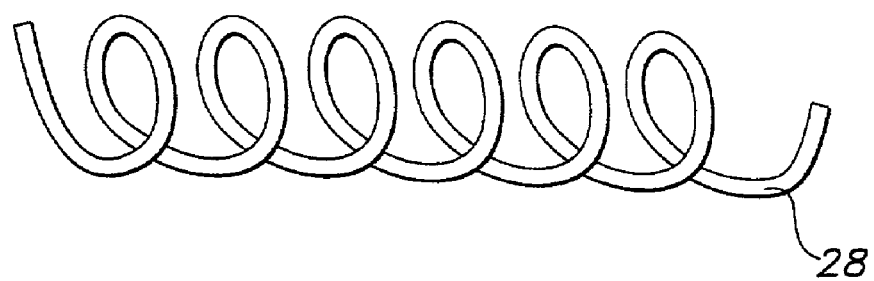
FIG. 5 is a perspective view of a helical coil formed of a single wound wire.
Figure 6:
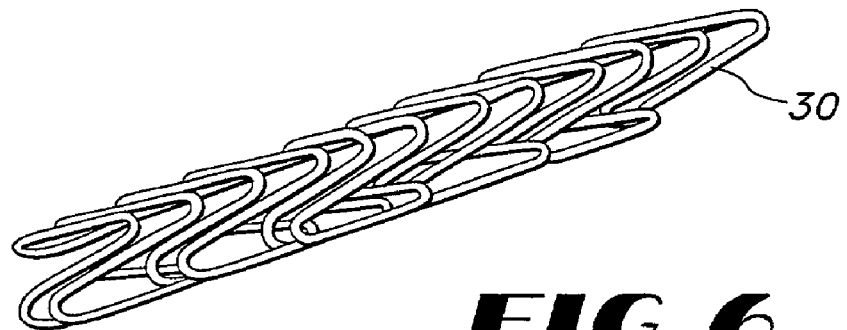
FIG. 6 is a perspective view of a stent having an elongate pre-helically coiled configuration.
Figure 7:
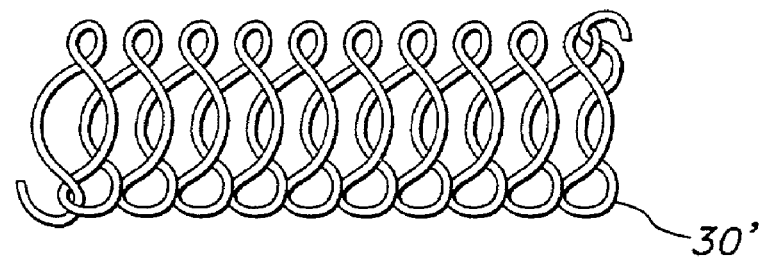
FIG. 7 is a perspective view of the stent of FIG. 6 in a radially expanded state.

Other useful stents capable of radial expansion are depicted in FIGS. 5, 6 and 7. As depicted in FIG. 5, stent 28 is a helical coil which is capable of achieving a radially expanded state (not shown). Stent 30, as depicted in FIG. 6, has an elongate pre-helically coiled configuration as shown by the waves of non-overlapping undulating windings. Stent 30 is capable of being radially expanded to expanded stent 30' as depicted in FIG. 7. These helically coiled or pre-helically stents are also useful with the practice of the present invention.

As used herein, the phrase "radially expandable stent" and it variants refer to a stent that is radially expandable from a quiescent state or radially contractible from an expanded state to a quiescent state. Such radially expandable stents may be self-expanding or require mechanical means, such as inflation by a balloon catheter, for expanding. Desirably, radially expandable stents that do not exhibit substantial longitudinal changes, such as less than about 50 linear percent longitudinal change, during the radial expansion or contraction are useful. The present invention, however, is not limited to the use of such stents with less than about 50 percent longitudinal shortening or lengthening.

As depicted in FIGS. 1 and 2, the stent-graft 10 of the present invention includes graft 12. In one aspect of the present invention the graft 12 is a vacuum deposited polymeric material. Desirably, the polymeric material is a poly-para-xylylene material. A poly-p-xylylene has the following repeating units:

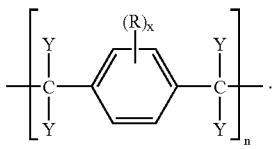

wherein n is 10–10,000, x is an integer from 0 to 4, Y, which can be the same or different, is hydrogen or halogen, and R is an aromatic nuclear substituent. Each substituent group R can be the same or different and can be any inert organic or inorganic group which can normally be substituted on aromatic nuclei. Such substituent groups include alkyl, aryl, alkenyl, amino, cyano, carboxyl, alkoxy, hydroxylalkyl, carbalkoxy and like radicals as well as inorganic radicals such as hydroxyl, nitro, halogen and other similar groups which are normally substitutable on aromatic nuclei. Desirably, the substituted groups are lower alkyl hydrocarbons, such as methyl, ethyl, propyl, butyl and hexyl; lower aryl hydrocarbons, such as phenyl, alkylated phenyl, naphthyl and like groups having no more than about 10 carbons; and halogen groups, such as chlorine, bromine, iodine and fluorine. More desirably, the substituted groups are chlorine groups.

Moreover, compositions having less than complete R group substitution, i.e., where x<4, are useful with the practice of the present invention. Desirably, the less than completely substituted materials include poly-para-xylylene; or Parylene N, wherein x equals 0 and Y equals hydrogen; poly-chloro-para-xylylene or Parylene C, wherein x equals 1, R represents chlorine and Y is hydrogen; and poly-dichloro-para-xylylene or Parylene D, wherein x equals 2, both R's represent chlorine and Y is hydrogen. These desirable materials are shown below, as follows:

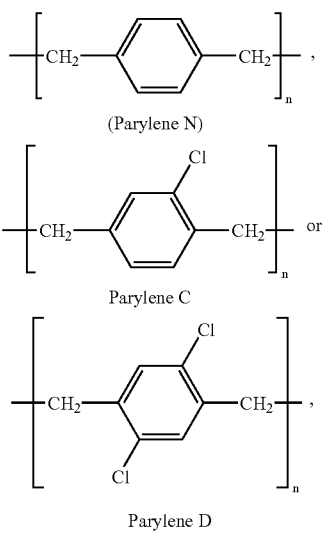

wherein n is as described above.

The above-described polymers may be formed by vaporization, pyrolysis and vapor deposition of a dimer or a di-para-xylylene having the following general formula:

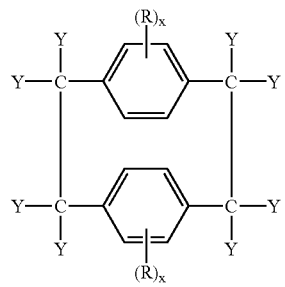

wherein Y, R and x are defined above and further wherein R can be the same or different and x can be the same or different. When R and/or x are different, a copolymer may be formed.

Desirably, the dimers include di-para-xylylene (dimer for parylene N), wherein x equals 0 and Y equals hydrogen; di-chloro-di-para-xylylene (dimer for Parylene C), wherein x equals 1, both R's represent chlorine and Y is hydrogen; and tetra-chloro-di-para-xylylene (dimer for Parylene D), wherein x equals 2, all R's represent chlorine and Y is hydrogen.

The above-described polymeric material may be formed from commercially available dimer compositions sold by Specialty Coating Systems, IN. Devices for the vacuum vapor deposition of the above-described poly-para-xylylenes are also available from Specialty Coating Systems, IN. Parylene, parylene N, parylene C and parylene D are generic names for the above-described linear poly-para-xylylene polymers.

The dimers are typically solid at room temperature. The dimers are first vaporized at a temperature of approximately 150° C. or greater. The vaporization may be done at any convenient pressure, but subatmospheric pressures are desirable. For instance pressures of 0.001 to 10 millimeters Hg are desirable. More desirably, the pressure is at about 1 millimeter Hg.

The pyrolysis of the vaporous di-para-xylylene dimers occurs upon heating the dimers from about 450° C. to about 700° C. The pyrolysis of the di-para-xylylene dimers begins at about 450° C. and involves the cleavage of the dimers at the two methylene-methylene bonds to yield monomeric diradical para-xylylene, as shown below.

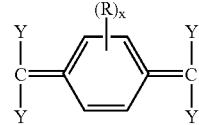

At temperatures above 700° C. cleavage of the constituent groups can occur resulting in a tri- or polyfunctional species causing cross linking or highly branched polymers. Desirably, a pyrolsis temperature of about 680° C. is used. It is desirable that reduced or subatmosphere pressures be employed during pyrolysis. Pressures within the range of 0.001 to 10 millimeters Hg are useful. Desirably, the pyrolysis pressure is slightly lower than the vaporization pressure. Desirably, a pyrolsis pressure of about 0.5 millimeters Hg is used. Furthermore, inert inorganic vapor diluents, such as nitrogen, argon, carbon dioxide and the like, can be employed to vary the temperature of operation or to change the total effective pressure of the system.

The diradicals formed in the manner described above are made to impinge upon a surface of a target material having a surface temperature below about 100° C. The temperature is advantageously below the condensation temperature of the diradicals present. The diradicals condense on the target surface and spontaneously polymerize thereat. A surface temperature of about room temperature or about 25° C. may suitably be used. The deposition is also typically done at a subatomspheric pressure, for instance about 0.001 to 10 millimeters Hg, or, desirably, at about 0.1 millimeters Hg.

The above-described subatmospheric pressures can be achieved by any convenient means, for instance through the use of a mechanical vacuum pump. A cold trap at about −70° C. is typically used to collect any non-deposited vaporous para-xylylenes.

Figure 8:
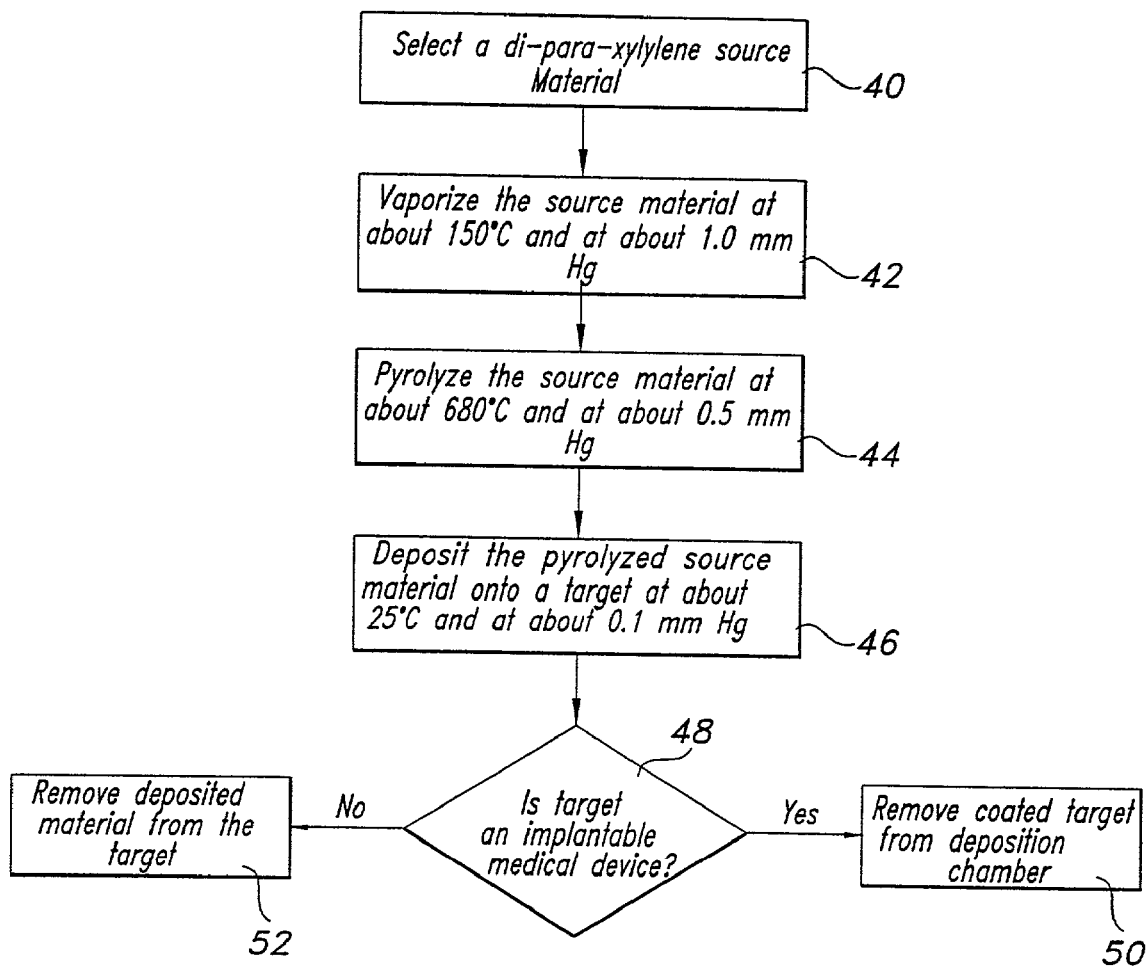
FIG. 8 depicts a flowchart of a method of the present invention.

FIG. 8 depicts a schematic flowchart for the method of the present invention for producing the inventive stent-graft. At step 40, a di-para-xylylene source material or dimer is selected. Desirably, the source materials or dimers include, but are not limited to, the above-described di-para-xylylene, di-chloro-di-para-xylylene, tetra-chloro-di-para-xylylene and combinations thereof. At step 42, the selected source material or dimer is vaporized. Desirably, the vaporization of the source material is at conditions described above, for instance at about 150° C. and at about 1.0 mm Hg. At step 44, the vaporized source material is pyrolyzed into diradicals. Desirably, the pyrolysis is at conditions described above, for instance at about 680° C. and at about 0.5 mm Hg. At step 46, the pyrolyzed source material is deposited onto a target. Desirably, the deposition is at room temperature and low pressure, for instance at about 25° C. and at about 0.1 mm Hg.

The deposited diradicals polymerize to form a poly-para-xylylene material. The deposition may be controlled to yield a material of any desirably thickness. For instance deposited material may be from about 5 microns to about 250 microns in thickness or depth. Desirably, the thickness of the deposited material is from about 10 microns to about 250 microns. More desirably, the thickness is from about 10 microns to about 100 microns. Even more desirably, the thickness is from about 10 microns to about 50 microns. As described below in further detail, a graft may be made of poly-para-xylylenes having a wall thickness of such dimensions.

Grafts having such thin walls of poly-para-xylylene are useful with the practice of the present invention. Tubes formed by extruding polymeric materials often have a wall thickness of several millimeters or several thousand microns. For example, even so-called thin tubes formed by extruding polytetrafluoroethylene often have a minimum wall thickness of 2 to 3 millimeters. Expanded polytetrafluoroethylene has been extruded to yield tubes with lower wall dimensions, such as about 200 microns or less. Such thin-walled expanded polytetrafluoroethylene tubes, however, are not self-supporting, i.e., they cannot maintain their tubular shape without some type of mechanical support. The lack of the self-supporting feature makes these tubes more difficult to process and handle as compared to self-supporting tubes.

In contrast, grafts of the present invention are thin-walled, i.e., less than 250 microns, and are self-supporting. Grafts of the present invention made from poly-para-xylylenes are self-supporting even with a wall thickness from about 10 to about 50 microns.

At steps 48 and 50, when the target is an implantable device, such as stent 14 of the present invention, the target is coated with a layer of poly-para-xylylene and removed from the deposition chamber. Advantageously, all exposed surfaces of the target are substantially coated with poly-para-xylylene. The thickness of the coating can be controlled to any desirable range, for instance from about 10 microns to about 50 microns.

Figure 9:
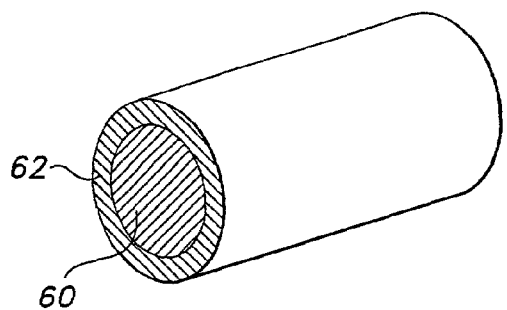
FIG. 9 is a perspective view of a mandrel having a deposited polymeric layer.
Figure 10:
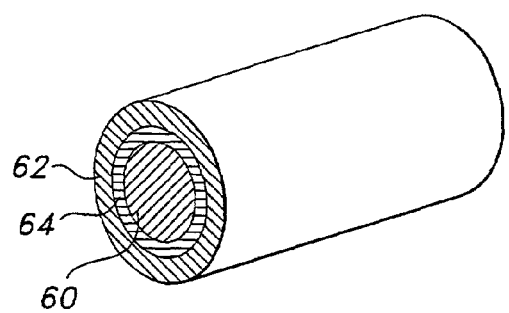
FIG. 10 is a perspective view of a mandrel having a deposited polymeric layer and further having a release layer therebetween.

At steps 48 and 52, when the target is not an implantable device, the deposited poly-para-xylylene is removed from the target. For example, as depicted in FIG. 9, graft 62, a substantially tubular structure, is deposited onto mandrel 60. Graft 62 is removed from mandrel 60 by any convenient means. For example, graft 62 may be simply slid off the mandrel 60. Alternatively, mandrel 60 may be a radially contractible mandrel, such as a length of silastic tubing. Upon contraction of the mandrel 60, the graft 62 is released therefrom. Advantageously, graft 62 is a self-supporting graft to facilitate its removal from the mandrel 60.

The present invention is not, however, limited to the use of contractible mandrels, and other mandrels may be suitable used. For example, mandrel 60 may be a rigid tube made from glass, metal or polymeric material. The mandrel 62 may have a coating of a release agent 64 on its surface to facilitate the removal of the graft 62 from the mandrel 60. The release agent 64 may be a lubricious material, such as a silicone, that permits the sliding disengagement of the graft 62 from mandrel 60. Alternatively, the release agent 64 may be a water soluble material that upon contact with water aids in the release of the graft 62 from the mandrel 60. A water soluble polymer, such as a polyacrylamide, may be suitably used. Other water soluble polymers include, but are not limited to, polyvinylalcohol, polyethylene oxide, polyethylene glycol, cellulose based polymers, polyvinyl pyrrolidone, polyvinylamine or polyetheleimine. Furthermore, the release agent 64, or even the mandrel 60, made be made from a low melting point material, such as a wax, which melts upon the application of low levels of heat to facilitate the removal of the graft 62. Even furthermore, the mandrel 60 may be dissolved by an acid thereby releasing the graft 62.

The poly-para-xylylene tubular structure or graft is used to form the stent-graft 10 of the present invention. Graft 12 may be disposed within stent 14 by slidingly engaging the two members as shown by the vectors in FIG. 2. Portions of stent 14 are securably attached to portions of graft 12 to form the stent-graft 10 of the present invention. Securement may be done by any convenient means. Desirably, the vapor deposition of additional poly-para-xylylene material is used to join portions of the stent 14 and the graft 12 to one and the other. Alternatively, an adhesive, such as a silicone or a urethane, may be used to adhesively bond such portions. Furthermore, such portions may be fused together through the use of heat, the use of a solvent, or combinations thereof. For example, parylene C may be dissolved in high boiling liquids, such as chloronaphthelene or benzolyl benzoate at temperatures above about 150° C. and used to bond the stent to the graft.

Moreover, securement of graft 12 and stent 14 may be accomplished through mechanical means. Desirably, such mechanical means do not puncture the graft 12. A locking ring may be disposed on one end or both ends of stent-graft 10, or even at portions thereinbetween. Such a locking ring may be placed over portions of the stent 14 and graft 12 and secured thereat. For example, a locking ring of poly-para-xylylene could be deposited or placed onto stent-graft 10. The locking ring could be physically attached thereto by any one of the above-described techniques, such as vapor deposition, adhesive bonding and fusing.

Figure 11:
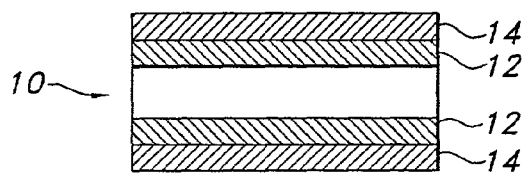
FIG. 11 is a cross-sectional view of the stent-graft of FIG. 1 taken along the 11—11 axis.
Figure 13:
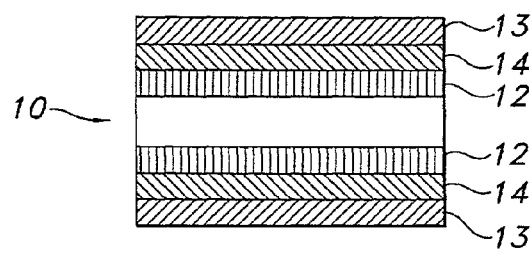
FIG. 13 is a cross-sectional view of yet another aspect of the present invention showing an exterior polymeric cover over a stent and an interior polymeric liner within the stent.
Figure 12:
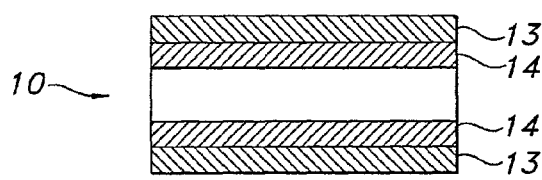
FIG. 12 is a cross-sectional view of another aspect of the stent-graft of the present invention showing an exterior polymeric cover over a stent.

FIG. 11 is a cross-sectional view of stent-graft 10 taken along the 11—11 axis showing graft 12 disposed within stent 14. In another aspect of the present invention, graft 13, as depicted in a cross-sectional view in FIG. 12, is disposed onto outer surfaces of stent 14. In yet another aspect of the present invention, stent-graft 10 includes a luminal graft 12, a stent 14 and an exterior graft 13, as depicted in a cross-sectional view in FIG. 11. Portions of grafts 12 and 13 and stent 14 may be securably attached to one and the other by any of the above-described techniques. In yet another aspect of the present invention a graft, such as graft 12, made from a poly-para-xylylene material by the above-described methods is useful as an implantable prosthesis. Such a graft is self-supporting while having a wall thickness only of about 10 microns to about 250 microns.

The invention may be further understood with reference to the following non-limiting examples.

EXAMPLES

Example 1

Parylene C Stent-graft

A tubular graft with a wall thick of about one half to one thousandth of an inch, or about 10 to 25 microns, was formed by vacuum vapor of parylene C. A dimer of di-chloro-di-p-xylylene, which is commercially available from Specialty Coating Systems, Inc., IN, was placed into a vaporization chamber within a vacuum deposition system. The pressure of the system was reduced to about 0.1 torr by means of a mechanical vacuum pump.

The dimer vaporized at about xylylene, 150° C. and at about 1.0 torr. The vaporized dimer entered a pyrolysis chamber. The pyrolysis chamber was at about 680° C. and about 0.5 torr. The vaporized dimer was pyrolyzed into diradicals. The diradicals entered a rotating deposition chamber having a mandrel. The deposition chamber was operated at about 25° C. and about 0.1 torr. The diradicals were directed towards the outer cylindrical surfaces of the mandrel. The outer cylindrical surface of the mandrel was completely coated with parylene C. The parylene coating was removed from the mandrel to produce a self-supporting graft.

A portion of the graft was placed on a mandrel. A radially expandable stent in its expanded state was placed over the graft. The mandrel containing the graft and the stent were placed in the deposition chamber. Additional parylene C was deposited. After removal from the deposition system the graft was securably attached to the stent by the additional deposited parylene material.

While the present invention was described as a stent-graft, other implantable devices are within the spirit of the present invention. For example, any implantable device having an open lattice and a poly-para-xylylene covering or lining over portions of the open lattice may be made by the practice of the present invention. For example, a carotid filter having an open lattice structure and having a base cone covered by a poly-para-xylylene cover having micro-drilled holes would be one example of such an implantable device. Moreover, the present is not limited to implantable devices, and any device, medical or non-medical, having a poly-para-xylylene coating or covering across an open cell may be made by the practice of the present invention.

Although illustrative aspects of the present invention have been described herein with reference to the accompanying drawings, it is to be understood that the invention is not limited to those precise aspects, and that various other changes and modifications may be effected therein by one skilled in the art without departing from the scope or spirit of the invention.

What is claimed is:
1. A stent-graft endoprosthesis comprising:
   a seamless tubular graft of biocompatible polymeric material having a wall thickness defining a luminal surface and an exterior surface;
   a radially expandable coated stent securably, circumferentially and axially disposed over said exterior surface, wherein said coated stent is coated with said biocompatible polymeric material, said stent being a metallic stent having an open lattice tubular structure;
   wherein said biocompatible polymeric material consists essentially of poly-para-xylylene having a formula of

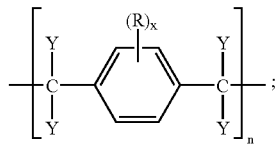

wherein n is from about 10 to about 10,000,
x is from 0 to 4,
R, which can be the same or different, is alkyl, aryl, alkenyl, amino, cyano, carboxyl, alkoxy, hydroxylalkyl, carbalkoxy, hydroxyl, nitro, chlorine, bromine, iodine and fluorine, and
Y, which can be the same or different, is hydrogen, chlorine, bromine, iodine and fluorine.

2. The endoprosthesis of claim 1 wherein Y is hydrogen, x is from 0 to 2 and, when x is 1 or 2, R is chlorine.

3. An implantable stent-graft device comprising:
   a seamless and self-supporting tubular non-textile graft of biocompatible polymeric material having a wall thickness of about 10 microns to about 100 microns defining a luminal surface and an exterior surface; and
   a radially expandable stent securably disposed over portion of said exterior surface, said stent being a metallic stent having an open lattice tubular structure
   wherein said polymeric material comprises poly-para-xylylene having a formula of

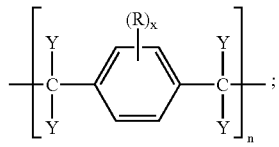

wherein n is from about 10 to about 10,000,
x is from 0 to 4,
R, which can be the same or different, is alkyl, aryl, alkenyl, amino, cyano, carboxyl, alkoxy, hydroxylalkyl, carbalkoxy, hydroxyl, nitro, chlorine, bromine, iodine and fluorine, and
Y, which can be the same or different, is hydrogen, chlorine, bromine, iodine and fluorine.

4. The device of claim 3 wherein said wall thickness is from about 10 microns to about 50 microns.

5. The endoprosthesis of claim 3 wherein Y is hydrogen, x is from 0 to 2 and, when x is 1 or 2, R is chlorine.

6. The endoprosthesis of claim 3 wherein said stent is coated with said poly-para-xylylene.

7. A stent-graft endoprosthesis comprising:
a seamless tubular non-textile graft of biocompatible polymeric material having a wall thickness of about 10 microns to about 250 microns defining a luminal surface and an exterior surface; and
a radially expandable stent securably disposed over portion of said exterior surface, said stent being a metallic stent having an open lattice tubular structure;
wherein said polymeric material comprises a poly-para-xylylene having a formula of

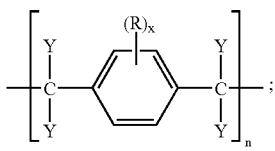

wherein n is from about 10 to about 10,000,
x is from 0 to 4,
R, which can be the same or different, is alkyl, aryl, alkenyl, amino, cyano, carboxyl, alkoxy, hydroxylalkyl, carbalkoxy, hydroxyl, nitro, chlorine, bromine, iodine and fluorine, and
Y, which can be the same or different, is hydrogen, chlorine, bromine, iodine and fluorine.

8. The endoprosthesis of claim 7 wherein Y is hydrogen, x is from 0 to 2 and, when x is 1 or 2, R is chlorine.

9. The endoprosthesis of claim 7 wherein said stent is coated said poly-para-xylylene.

10. A stent-graft endoprosthesis comprising:
a seamless tubular non-textile graft of biocompatible polymeric material having a wall thickness defining a luminal surface and an exterior surface; and
a radially expandable stent securably disposed over a portion of said exterior surface, said stent being a metallic stent having an open lattice tubular structure;
wherein said polymeric material consists essentially of a poly-para-xylylene having a formula of

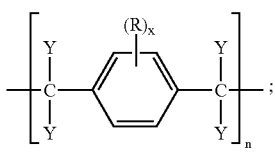

wherein n is from about 10 to about 10,000,
x is from 0 to 4,
R, which can be the same or different, is alkyl, aryl, alkenyl, amino, cyano, carboxyl, alkoxy, hydroxylalkyl, carbalkoxy, hydroxyl, nitro, chlorine, bromine, iodine and fluorine, and
Y, which can be the same or different, is hydrogen, chlorine, bromine, iodine and fluorine.

11. The endoprosthesis of claim 10 wherein Y is hydrogen, x is from 0 to 2 and, when x is 1 or 2, R is chlorine.

12. The endoprosthesis of claim 10 wherein said wall thickness is from about 10 microns to about 250 microns.

13. The endoprosthesis of claim 10 wherein said stent is coated with said poly-para-xylylene.

14. The endoprosthesis of claim 10 further comprising a second seamless tubular graft of said polymeric material having a wall thickness defining an interior surface and an exterior surface; wherein said second graft is securably disposed over said stent to form an outer polymeric cover thereover.

15. A method for producing a stent-graft endoprosthesis composing:
providing a mandrel having a cylindrical outer surface;
depositing a poly-para-xylylene polymer onto a portion of said outer surface of said mandrel to form a tubular polymeric graft having a wall thickness defining a luminal surface and an exterior surface of said graft;
providing a radially expandable metallic stent having an open lattice tubular structure; and
securing portions of said stent to portions of said outer surface of said graft to form said stent-graft endoprosthesis.

16. The method of claim 15 wherein said poly-para-xylylene polymer comprises a polymer having a formula of

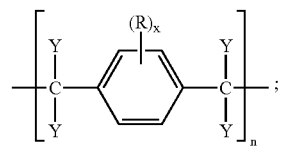

wherein n is from about 10 to about 10,000,
x is from 0 to 4,
R, which can be the same or different, is alkyl, aryl, alkenyl, amino, cyano, carboxyl, alkoxy, hydroxylalkyl, carbalkoxy, hydroxyl, nitro, chlorine, bromine, iodine and fluorine, and
Y, which can be the same or different, is hydrogen, chlorine, bromine, iodine and fluorine.

17. The endoprosthesis of claim 16 wherein Y is hydrogen, x is from 0 to 2 and, when x is 1 or 2, R is chlorine.

18. The method of claim 15 further comprising:
coating said stent with said poly-para-xylylene polymer.

19. The method of claim 15 wherein said securing includes adhesive bonding, thermal fusing; solvent fusing and mechanical attaching.

20. The method of claim 15 wherein said depositing further comprises depositing said poly-para-xylylene polymer until said thickness is from about 10 microns to about 250 microns.

21. The method of claim 15 wherein said depositing further comprises:
providing a poly-para-xylylene source dimer material;
vaporizing said dimer material;
pyrolyzing said dimer material to yield poly-para-xylylene precursors;
vapor depositing said precursors onto said mandrel; and
polymerizing said precursors to yield said poly-para-xylylene polymer.

22. The method of claim 21 wherein said poly-para-xylylene precursors are selected from the group consisting of di-para-xylylene, di-chloro-di-para-xylylene, tetrachloro-di-para-xylylene and combinations thereof; and further wherein said poly-para-xylylene polymer is selected from the group consisting of parylene C, parylene D, parylene N and combinations thereof.

23. The method of claim 15 further comprising removing said graft from said mandrel.

24. The method of claim 15 further comprising removing said stent-graft endoprosthesis from said mandrel.

25. The method of claim 15 said providing said radially expandable stent further comprises:
   radially expanding said stent; and
   positioning said radially expanded stent over said graft.

26. A method for producing a stent-graft endoprosthesis comprising:
   providing a tubular graft of vacuum vapor deposited poly-para-xylylene polymer;
   providing a radially expandable metallic stent having an open lattice tubular structure; and
   securing portions of said stent to portions of said outer surface of said graft to form said stent-graft endoprosthesis.

27. The method of claim 26 wherein said polymer is selected from the group consisting of parylene N, parylene D, parylene C and combinations thereof.

28. An endoprosthesis consisting essentially of:
   a seamless tubular non-textile graft of biocompatible polymeric material having a wall thickness of about 10 microns to about 250 microns defining a luminal surface and an exterior surface;
   wherein said polymeric material is a poly-para-xylylene having a formula of

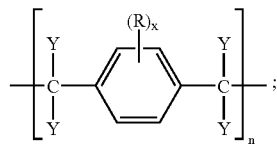

wherein n is from about 10 to about 10,000,
   x is from 0 to 4,
   R, which can be the same or different, is alkyl, aryl, alkenyl, amino, cyano, carboxyl, alkoxy, hydroxylalkyl, carbalkoxy, hydroxyl, nitro, chlorine, bromine, iodine and fluorine, and
   Y, which can be the same or different, is hydrogen, chlorine, bromine, iodine and fluorine.

29. The endoprosthesis of claim 28 wherein Y is hydrogen, x is from 0 to 2 and, when x is 1 or 2, R is chlorine.

* * * * *